United States Patent [19]

Olvey

[11] Patent Number: 5,110,345
[45] Date of Patent: May 5, 1992

[54] PROCESS FOR THE HYBRIDIZATION OF COTTON

[75] Inventor: James M. Olvey, Tucson, Ariz.

[73] Assignee: University Patents, Inc., Westport, Conn.

[21] Appl. No.: 2,192

[22] Filed: Jan. 12, 1987

Related U.S. Application Data

[63] Continuation of Ser. No. 710,521, Mar. 12, 1985, abandoned, which is a continuation of Ser. No. 337,153, Jan. 5, 1982, abandoned.

[51] Int. Cl.$^5$ .............................................. A01N 43/80
[52] U.S. Cl. ................................................ 71/90; 71/65
[58] Field of Search ................................................ 71/90

[56] References Cited

U.S. PATENT DOCUMENTS

| | | | |
|---|---|---|---|
| 3,341,547 | 9/1967 | Mailey | 260/302 |
| 3,393,992 | 1/1968 | Mailey | 71/90 |
| 4,380,465 | 4/1983 | Howe et al. | 71/90 |

FOREIGN PATENT DOCUMENTS

| | | |
|---|---|---|
| 0002859 | 4/1979 | European Pat. Off. |
| 2641295 | 3/1977 | Fed. Rep. of Germany |
| 7116163 | 5/1972 | Netherlands |

OTHER PUBLICATIONS

Olvey et al., Proceedings of the Beltwide Cotton Production Research Conference, p. 84 (1981).
Olvey, The Cotton Belt Tour (1979).
"Chemically Induced Male Sterility, a New Tool in Plant Breeding", F. Wit. *Euphytica*, vol. 9, No. 1, pp. 1 et. seq. (1960).
"Evaluation of Certain Chemicals as Selective Gametocides for Wheat", Porter et al, *Crop science*, pp. 381 et seq. (1961).
"Effects of Sodium 2,3-dichloroisobutyrate on Six Characteristics of American Upland Cotton", Richmond, *Crop Science*, p. 58 (1961).
"Termination of Late Season Cotton Fruiting with Plant Growth Regulators", Kittock et al., *Crop Science*, vol. 17, No. 7, pp. 320-324.
Pennwalt Technical Data Sheet for TD-1123, May 15, 1978.
Shaver et al., "Fate of Potassium Etc.", (1979), J. Ag. Food Chem 27, pp. 325-328.
Cathy, "Evaluation of Potassium, etc.", (1978), CA 89 No. 101679a (1978).
"Growth and Development of the Cotton Plant in Arizona", Dennis et al., U. of Arizona pamphlet 8168.
Kittock et al., "Timing Late-Season Fruiting, etc.,", CA 93: 108841; 1980.
"Effect of Growth-Stimulant Acids on the Economic Characters of Intraspecific Hybrids of Cottom": Vopr. Genet., selektsii i semenovodstva khlopchatnika i lyutserny, 13, Eshankhodshaev, T., Publ: Tashkent, Uzbek SSR, 1976, 130-135 (in Russian).
"Practical Works with the Selection and Seed-Forming of Agricultural Plants", Moscow, Kolos publishers, 1976, pp. 131 et seq.; "Praktikum po selektsii i semenovodstvu polevykhl Kultur", moskva, "Kolos", 1976, s. 131.

*Primary Examiner*—Glennon H. Hollrah
*Assistant Examiner*—B. Bembenick
*Attorney, Agent, or Firm*—Woodcock Washburn Kurtz Mackiewicz & Norris

[57] ABSTRACT

Methods are disclosed for rendering cotton plants male sterile through application of isothiazole plant growth regulators without causing substantial female sterility or loss of reproductive vigor. Processes for effecting the hybridization of cotton employing monitoring of the degree of burning of cotton bracts are presented. More particularly, male sterility is attained by the application of potassium 3,4-dichloroisothiazole-5-carboxylate to cotton plants in an amount sufficient to cause finger burning of the bracts without causing excess burning thereof. Hybridization is attained by exposing male sterile plants in accordance with the foregoing processes to pollen from plants of differing varieties of cotton.

22 Claims, 1 Drawing Sheet

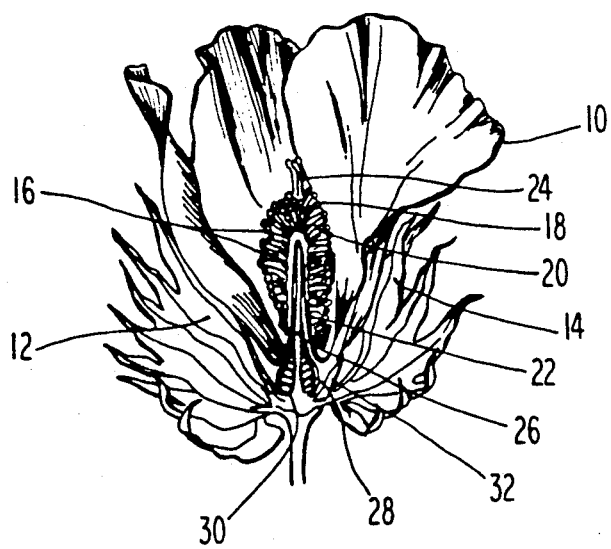
*Fig. 1*
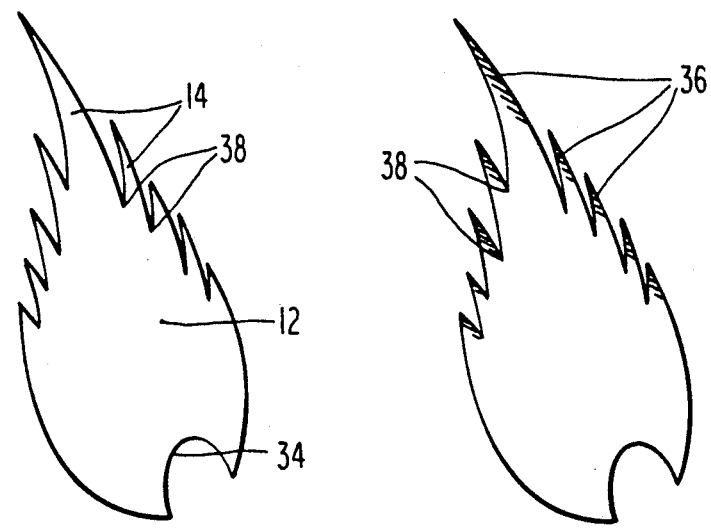
*Fig. 2A*  *Fig. 2B*
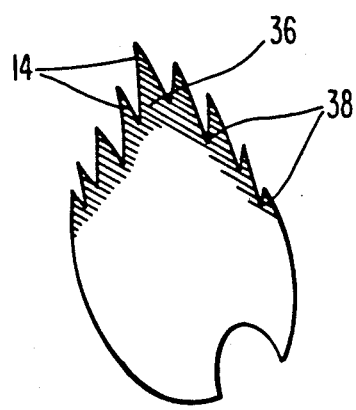  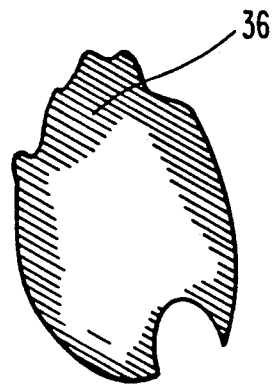
*Fig. 2C*  *Fig. 2D*

PROCESS FOR THE HYBRIDIZATION OF COTTON

This is a continuation of application Ser. No. 710,521, filed Mar. 12, 1985, now abandoned which is a continuation of application Ser. No. 337,153 filed Jan. 5, 1982, now abandoned.

BACKGROUND OF THE INVENTION

Hybridization of plant and animal species has long been known to be a desirable means for improving the physical and productive qualities of crops and livestock. The benefits to be obtained from selective cross-breeding are manifold and are well known to agriculturalists. Some families of plants, however, are presently not conveniently susceptible to hybridization. These include plants such as cotton which are self-pollenating and in which sexual maturity arrives simultaneously for both the male and female sexual organs within a flower. In view of the high commercial utility and value of cotton to the agricultural community, means for the hybridization of cotton have long been sought.

Since the principal economic impact of cotton plants lies in the production of cotton fiber from bolls, it is desirable to produce hybrid cotton seeds capable of maturing into cotton plants having larger, more numerous, and more productive cotton bolls. It is similarly desired to produce cotton fiber having improved manufacturing and processing qualities.

Presently, the only system of achieving hybridization in cotton which is believed to have any significant commercial potential is a method known to those skilled in the art as the "cytoplasmic male sterility-restorer method." This technique has certain significant, inherent disadvantages including the lack of an adequate "restorer" system for genetic restoration of fertility in the hybrid.

Chemically induced male sterilization has been employed in some plant families to effect hybridization. Thus, rows or groups of plants are selected to become the female host plants for the production of hybrid seeds. These female hosts are rendered male sterile by contact with a selective chemical sterilant. Such rows or groups are interposed with rows or groups of plants selected to perform as male donor plants. Such male donors are not contacted with the chemical sterilant and produce pollen in the normal fashion. This pollen is allowed to contact the female sexual organs of the male sterile female hosts either through wind pollination, hand pollination or through the mediation of insects. If the female hosts are effectively male sterile, self-pollination of such hosts is precluded and uniform, exclusive pollination of such female hosts by the selected male donor plants is ensured. The seeds resulting from such cross-pollination are hybrid in nature and reflect differing male and female parental heritages. Such seeds, when planted and nurtured during subsequent growing cycles, may exhibit hybrid vigor, improved physical traits, and other benefits known to be associated with such hybrid genetics. See in this regard "Chemically Induced Male Sterility, a New Tool in Plant Breeding?" F. Wit. *Euphytica* Vol. 9, No. 1 p. 1 et. seq. (1960) and "Evaluation of Certain Chemicals as Selective Gametocides for Wheat", Porter et al. *Crop Science* p. 381 et. seq. (1961).

Chemical sterilants have heretofor been proposed for use in the hybridization of cotton. One such composition is Dalapon (Dow Company), believed to be a 2,2-dichloropropanoic acid. While Dalapon will promote male sterility in cotton plants, it also spurs vegetative growth of the plants at the expense of reproductive vigor. Cotton plants treated with this material exhibit low flower counts and develop few mature bolls thus evidencing diminished female fertility. Accordingly, Dalapon is considered to be commercially ineffective for use in the hybridization of cotton. A chemically similar material 2,3-dichloroisobutyrate (FW-450 of the Rohm and Haas Co.) which has also been reported to have gametocidic activity in cotton, is also believed to share shortcomings similar to Dalapon's. See "Effects of Sodium 2,3-dichloroisobutyrate on Six Characteristics of American Upland Cotton" Richmond, *Crop Science*, p. 58 (1961).

Pennwalt Corporation's TD 1123 plant growth regulator, which is potassium 3,4-dichloro-5-isothiazole carboxylate, has been suggested for use in late season termination for insect control in cotton and as a conditioner for defoliation. See "Termination of Late Season Cotton Fruiting with Plant Growth Regulators" Kittock et. al., *Crop Science* Vol. 17 No. 7 pp. 320–24 (1977) and U.S. Pat. No. 3,341,547 issued to Malley. It has also been suggested that TD 1123 may act as a selective male gametocide for cotton. See, for example, Olvey et al pre-conference brochure of the 1981 Beltwide Cotton Production Research Conferences and Special Meetings, p. 9. No method for attaining effective male sterility in cotton while maintaining good female fertility has been disclosed heretofore, however. Furthermore, no effective methods for the hybridization of cotton are known.

SUMMARY OF THE INVENTION

Methods for the commercially feasible hybridization of cotton are provided for the first time. More particularly, it has been found that by maintainance of levels of isothiazole plant growth regulators within limited ranges within cotton plants, effective male sterility therein may be attained without undo loss of female fertility or of reproductive vigor. Such levels may be conveniently maintained within cotton plants through monitoring of the degree of burning of the bracts of cotton flowers subsequent to the application of isothiazole growth regulator and the adjusting of the rate or periodicity of application performed as needed in response to the monitoring. Exposure of cotton plants rendered male sterile in accordance with this process to pollen from a second variety of cotton produces hybrid cotton seed. Subsequent cultivation of the hybrid seed yields hybrid cotton plants producing cotton fiber, which plants exhibit hybrid vigor and other beneficial qualities.

OBJECTS OF THE INVENTION

It is an object of this invention to provide methods for the hybridization of plants, especially cotton plants.

It is another object to provide methods for inducing male sterility in cotton plants while maintaining reproductive vigor and female fertility.

A further object is to provide such processes which are at once effective, convenient, inexpensive, and commercially feasible.

Yet another object is to provide such procedures for hybridizing cotton employing a male sterilant.

A further object is to provide such procedures which employ an isothiazole plant growth regulator such as TD-1123.

A further object is to provide a procedure for monitoring the level of isothiazole plant growth regulators such as TD-1123 in cotton plants and for ascertaining whether a level effective for producing male sterility without impairing female fertility or reproductive vigor has been attained.

An additional object is to provide a regulatory mechanism for the application of isothiazole plant growth regulators to cotton which permits attainment of male sterility for substantially an effective cotton reproductive season while maintaining good female fertility.

Yet another object is to produce cotton seeds of hybrid origin.

A further object is the cultivation of cotton exhibiting one or more hybrid traits and the isolation of cotton fiber therefrom.

An additional object is to provide effective male sterilant compositions for cotton.

These and other objects will be apparent from a review of the present specification.

DESCRIPTION OF THE DRAWINGS

FIG. 1 is a partial cross-sectional rendering of a cotton flower depicting inter alia, the male and female sexual organs and the bracts.

FIG. 2a is a view of a normal cotton flower bract.

FIG. 2b portrays a cotton bract which has a sensible degree of finger burning.

FIG. 2c shows a bract having extensive finger burning which extends somewhat beyond the inter-finger gaps.

FIG. 2d portrays a cotton bract wherein burning is excessive and has passed beyond finger burning.

DETAILED DESCRIPTION OF THE INVENTION

Isothiazole plant growth regulators such as salts of 3,4-dichloroisothiazole-5-carboxylic acid and related compositions, produced by the Pennwalt Corporation as a potassium salt under the denomination TD-1123, have been found to be effective, selective male sterilants for upland cotton when applied in quantities and according to the schedules disclosed by the present invention. One process leading to the preparation of TD-1123 is described in U.S. Pat. No. 3,341,547 issued to Malley. It is vital to the success of the present process for hybridization of cotton that an amount of isothiazole growth regulator be applied which renders the subject plants effectively male sterile without causing excessive phytotoxicity or female sterility. In "Fate of Potassium 3,4-dichloro-5-isothiazolecarboxylate in Cotton Plants and White Rats," Shaver et. al., *J. Agricultural Food Chem.*, Vol. 27, No. 2, pp. 325328 (1979), it was reported that a high proportion of radioactive carbon labeled TD-1123 accumulated in bracts of cotton flowers on a weight basis. This concentration was found to be second only to the concentration found in the seeds of treated plants. It has now been found that biological evaluation of the concentration of isothiazole growth regulators in the bracts of cotton may be employed in a process for the selective male sterilization of such cotton as an indicator for the sufficiency of application of isothiazole growth regulators and as a warning of excess application thereof.

A cotton flower is depicted in FIG. 1. A collection of petals 10 is surrounded by a trio of bracts 12 having a plurality of fingers 14 thereupon. The petals serve to contain and protect the male and female sexual organs of the cotton flower and to attract insect pollination media thereto. Thus, the male sexual organs are represented by pollen-producing stamens 16 each comprising an anther 18 located on a filament 20. Each of the 90 to 100 stamens of the cotton flower is attached to a staminal column 22. The female portion of a cotton flower comprises the pistil composed of the stigma 24, style 26, and ovary 28. The ovary contains a plurality of ovules 30. The cotton flower also comprises a calyx 32 located between the bracts and the petals. The foregoing description has been adapted from "Growth and Development of the Cotton Plant in Arizona," Dennis et. al., U. of Ariz. pamphlet 8168, which is incorporated by reference herein.

FIG. 2a shows a bract in greater detail. Thus, the bract 12 and its fingers 14 are more clearly presented. The inter-finger gaps, 38 are shown. The bract has been removed from the base of the cotton flower at the position indicated by reference number 34. No burning is evidenced in this figure.

FIG. 2b portrays a bract exhibiting some finger burning. Thus, crosshatching, 36 indicates areas of browning, wilting or other evidence of phytotoxicity localized on the fingers.

FIG. 2c discloses a bract which has undergone extensive finger burning in accordance with the practice of the processes of this invention. Thus, the fingers 14 have been somewhat eroded in size. An area of browning, wrinkling, or other evidence of local phytotoxicity is indicated by crosshatching 36. In this figure, the burning involves most or all of the fingers 14 of the bract and has extended somewhat into the main body portion of the bract beyond the inter-finger gaps, 38 of the bract.

FIG. 2d shows an extensively burned bract such as would be the result of an application of an excessive amount of isothiazole growth regulator to a cotton plant. Thus, the fingers have been largely eroded or burned away and an extensive portion of the main bract body beyond the inter-finger gap region has been involved with browning or other evidence of local phytotoxicity, 36. Excessive burning such as depicted in FIG. 2d would be evidence of the application of an excessive amount of isothiazole growth regulator and would imply either loss of reproductive vigor, excessive decline in female fertility, or excessive phytotoxicity generally to the plant.

Cotton plants may be rendered male sterile while retaining substantial female fertility in accordance with the present invention by contacting the plants with an isothiazole growth regulator followed by monitoring the presence or absence and degree of "burning" of the developing bracts of the plant and by adjusting the amount of isothiazole applied to the plants in response to the monitoring.

As used herein, an isothiazole plant growth regulator is a member of the class of isothiazoles which is capable of modifying the growth rate or pattern of a cotton plant in a predictable way in commercially reasonable doses. Such regulators are generally those which have a 5-carboxylate function. The preeminant isothiazole plant growth regulator is Pennwalt's TD 1123. More particularly, when sufficient isothiazole plant growth regulator such as TD-1123 is applied to cotton plants such that the bracts which subsequently develop on the plant exhibit a sensible degree of "burning" of the finger region —finger burning—then that amount of regulator is sufficient to render the plant male sterile for a period of time. When, however, an amount of regulator is administered to a cotton plant such that the bracts are burned extensively in areas beyond the inter-finger gaps—denominated excessive burning—then such an amount will result in objectionable degrees of female infertility, loss of reproductive vigor, or overall plant phytotoxicity in addition to rendering the plant male sterile.

When an amount of isothiazole plant growth regulator is administered to cotton plants which is insufficient to result in effective male sterility of the plants, then the bracts will exhibit substantially no burning.

It will be appreciated that a continuum exists between states of relative non-burning, states of finger burning according to this invention, and states of excessive burning of the bracts of cotton plants treated with isothiazole plant growth regulators. It is believed that those skilled in the art will have no difficulty, after routine experimentation, in acquainting themselves with that degree of burning which is optimum to provide male sterility without incurring female sterility or other detrimental effects. It will similarly be appreciated that as increasing amount of burning is evidenced on the bracts of cotton plants, that increasing tendencies towards female sterility, loss of reproductive vigor and general phytotoxicity will occur. In general, therefore, finger burning as used in this specification will mean any sensible degree of burning of the fingers of the bracts of a cotton flower which is less than that degree of burning which progresses substantially inwardly of the inter-finger gaps of the bract. That degree of burning depicted in FIG. 2c is intended to represent an approximation of the maximum amount of burning inwardly of the inter-finger gaps, which burning falls within the definition of "finger burning" for most cotton varieties in accordance with this invention. In this regard, however, it will be noted that some burning inwardly of the inter-finger gaps may be exhibited. This burning is far less than the burning exhibited by FIG. 2d wherein substantial involvement inwardly of the inter-finger gaps occurs. It must further be emphasized that finger burning is intended as a qualitative rather than a quantitative term. It is believed, that those skilled in the art will have no difficulty in rendering the requirements of finger burning into ordinary practice. It should also be noted that the burning of the bracts need not be symmetric and that an average degree of burning may be employed to determine compliance with the spirit of this invention as described herein.

According to the practice of the present invention, it is preferred that an amount of an isothiazole plant growth regulator such as TD-1123 be applied to cotton plants, the degree of bract burning be subsequently determined, and the amount of isothiazole altered if necessary in response to the monitoring of the degree of bract burning. In general, it has been found that an application of about 0.1 to about 2.0 lb./acre of TD-1123 measured as active ingredient topically applied such as by a ground level foliar spray is sufficient to cause male sterilization without accomplishing female sterility and, accordingly, to cause bract finger burning without excessive burning. It has also been found that TD-1123 may be applied to cotton through irrigation water. In such cases, however, a 10 to 100 fold increase in amount is required to attain the same level of male sterility as may be had with topical sprays. As will be set forth hereinafter, the amount of isothiazole to be applied will vary depending upon the mass of the plants to be treated and, accordingly, with the particular time in the growing season exact at the time of treatment.

The bracts of cotton plants treated with TD-1123 should be monitored from three to five days after the application of the chemical. In three days, indications of the degree of developing burning of the bracts will be exhibited. In five days, the extent of burning will have been indicated clearly. If it is found that no finger burning of the bracts has occurred subsequent to application of the isothiazole, then an additional application may be made, a subsequent monitoring of the bract burning undertaken and further modification of the application of isothiazole performed if necessary. If sufficient chemical has been applied to result in finger burning without excessive burning of the bract, then no additional application of TD-1123 need be made and the status need only be maintained. If, however, monitoring of the bracts subsequent to application of TD-1123 indicates that an excessive amount has been applied as evidenced by excessive bract burning then moderation of the effects of the successive application may be had such as by the application of irrigation water to the plants. It is believed that the usual growth spurt found in cotton which has been irrigated will effectively dilute the concentration of TD-1123 internal to the plant and cause it to return to a more desirable level as reflected by bract burn monitoring. Subsequent monitoring of the developing bracts will indicate whether sufficient dilution of the excess TD-1123 has occurred (through the increase in plant mass) or whether additional irrigation procedures are warranted. Alternatively, subsequently scheduled applications of growth regulator may be altered in amount or in timing to effect such moderation. In general, it will be appreciated that, through a monitoring of the degree of burning of the bracts of cotton flowers, a feedback loop may be attained whereby the proper application of TD-1123 may be established and maintained.

It has been found that a period of time of approximately two weeks is necessary to render a cotton plant male sterile subsequent to the application of an effective amount of TD-1123. It has also been found that the period of male sterility extends from about 2-4 weeks subsequent to the application. Accordingly, periodic application of an isothiazole growth regulator such as TD-1123 is preferred in order to afford substantially continuous male sterility in cotton plants. A periodicity of application of approximately two weeks has been found to be effective for TD 1123. Similar periods of time are believed to be applicable to the employment of other isothiazole plant growth regulators. Monitoring of the degree of bract burning should be accomplished and modification of the amount and/or periodicity of application of growth regulator undertaken in response to the monitoring to ensure that a sufficient amount of isothiazole is maintained within the cotton plant without creating an excess. Modification of the amount and/or periodicity of application of the chemical in response to this monitoring is desired to facilitate this goal.

It will be appreciated that the amount of isothiazole growth regulator which is necessary for the attainment of finger burning without excessive burning of the bracts of cotton plants will vary depending upon the degree of maturation of those plants. Thus, very small plants, plants early in a growing season, require lesser quantities of such regulators than do more mature, larger plants. Such quantities will also vary depending upon cotton type, climate, weather, the isothiazole, and other factors. For upland cotton grown in Arizona, it has been found that the amounts of TD 1123 measured as active ingredient sufficient to cause finger burning and male sterility may be estimated as follows:

mid May from about 0.1 to about 0.2 lb/acre
mid June from about 0.5 to about 1.0 lb/acre
early July from about 0.5 to about 1.5 lb/acre
therinafter from about 1.0 to about 2.0 lb/acre It is believed that those skilled in the art will have no difficulty in determining proper application rates for a particular combination of factors after routine experimentation. Overall, application rates of from about 0.1 to about 2.0 lb/acre will be employed.

It is possible to render cotton plants male sterile for an effective reproductive season. Thus, an initial application of TD-1123 or other isothiazole is made to cotton plants approximately two to three weeks prior to first flowering. Since the cotton plants are rendered male sterile approximately two to three weeks after the application of TD-1123, such sterility coincides with first flowering. Periodic application of additional quantities of isothiazole growth regulator on a schedule of approximately two weeks will ensure that continuous sterility obtains. In general, it is permissible to terminate application of sterilant about 12 weeks prior to the projected harvest of the plants. This is possible because any male fertile flowers which may be formed subsequent to the last application of the season will have insufficient time to mature prior to the harvest.

Hybridization of a first variety of cotton with a second cotton variety may be attained. Thus, an isothiazole is periodically applied to plants of the first variety to render them male sterile. Such sterility is assured through monitoring of the bract burning and adjustment of the amount or periodicity of isothiazole application as described hereinabove. Such monitoring also assures maintenance of female fertility in the plants of the first variety through avoidance of excess application. Such male sterile plants are then exposed to pollen from the second variety of cotton, allowed to mature and harvested to provide hybrid seed. It is preferred that the plants of the first variety be maintained in a male sterile condition for an entire reproductive season so as to preclude the isolation of non-hybrid seeds. The hybrid seed may subsequently be cultivated to produce plants bearing cotton.

The amount of isothiazole to be applied to a type of cotton plant together with the periodicity of application will vary with type or variety of cotton to be treated, the identity of the isothiazole growth regulator, temperature, climate, degree of natural rainfall, and many other factors. It is believed, however, that the burning response of cotton bracts as disclosed in the present specification will provide a reliable guide for the determination of adequacy of application under a given circumstance. Accordingly, it will be appreciated that the time of application prior to first flowering may vary from cotton variety to variety and under different climate conditions. Similarly, other temporal and quantitative specifications disclosed herein may vary as the foregoing variables are altered; such variability is foreseen. It is believed to be well within the routine skill of those skilled in the cultivation of cotton to determine rates of application, scheduling, and other variables from an understanding of the present inventive processes after routine experimentation.

Table 1 and 2 illustrates the effects of application of TD 1123 on various characteristics of upland cotton grown in Arizona. Also presented are similar data for Dalapon. Thus, single applications of TD 1123 and Dalapon were made at the varying, indicated, rates on Jul. 2, 1979. Evaluation of the duration of male sterility, percent set, flower count and other factors were then performed. For those data listed in Table 2, a moiety of plants were harvested on July 16 and Aug. 6, 1979.

Table 1 indicates that for an application of TD 1123 in early July in Arizona, it is preferred to employ rates of application between about 0.5 and 1.5 lb/acre. Such rates of application, as reflected in the data enclosed by dashed lines, result in finger burning without excessive burning of the bracts. Effective male sterility with maintainance of female fertility is reflected by the data for "100% male sterile and female fertile", "% set" and "Aug. # flowers/plot". This data is superior to that for Dalapon.

TABLE 1

Effects of TD-1123 on Various Characteristics of Upland Cotton

| Treatment | Rate (lbs/Acre) | # Days 100% Male Sterile | 100% Male Sterile + Female Fertile | Leaf Phyto. | % Set | % Seed Emerg. | Avg. # Flowers/Plot | Grams Per Boll | Bolls Per Lb. | Seed Index | Seeds Per Boll |
|---|---|---|---|---|---|---|---|---|---|---|---|
| Control | 0 | 0 | 0 | None | 47 | 98 | 87.3 | 3.5 | 130 | 7.8 | 25.8 |
| Dala- | 1.73 | 4 | 4 | None | 65 | 95 | 56.0 | 3.2 | 142 | 8.8 | 20.8 |
| pon | 2.64 | 10 | 5 | Slight | 26 | 96 | 53.2 | 3.0 | 151 | 6.7 | 19.6 |
|  | 6.09 | 17 | 11 | Moderate | 35 | 86 | 17.8 | 1.9 | 239 | 7.2 | 13.5 |
|  | 12.69 | 25+ | 14 | Severe | 32 | — | 11.2 | 1.2 | 400 | 8.4 | 7.5 |
| TD-1123 | 0.04 | 0 | 0 | None | 23 | 98 | 76.7 | 3.4 | 133 | 8.1 | 24.8 |
|  | 0.09 | 0 | 0 | None | 33 | 96 | 81.2 | 3.4 | 133 | 8.5 | 23.5 |
|  | 0.17 | 0 | 0 | Slight | 35 | 98 | 88.0 | 3.4 | 133 | 8.1 | 25.5 |
|  | 0.42 | 2 | 2 | Slight | 63 | 93 | 94.7 | 3.4 | 133 | 8.1 | 24.1 |
|  | 0.65 | 12 | 11 | Slight | 55 | 94 | 107.7 | 2.8 | 162 | 8.3 | 19.8 |
|  | 0.81 | 12 | 11 | Slight | 50 | 93 | 92.9 | 2.8 | 162 | 8.0 | 20.4 |
|  | 1.07 | 18 | 15 | Mod. Severe | 34 | 97 | 90.9 | 2.8 | 162 | 7.8 | 20.7 |
|  | 1.10 | 15 | 15 | Moderate | 48 | 97 | 98.9 | 2.4 | 189 | 7.9 | 17.5 |
|  | 1.46 | 22 | 14 | Mod. Severe | 34 | 93 | 79.4 | 1.9 | 239 | 8.2 | 13.6 |
|  | 1.47 | 18 | 17 | Mod. Severe | 49 | 91 | 108.0 | 1.9 | 239 | 7.9 | 17.5 |
|  | 1.52 | 23 | 16 | Mod. Severe | 28 | 91 | 72.5 | 2.0 | 227 | 7.8 | 20.7 |
|  | 3.00 | 23+ | 0 | Severe | 20 | — | 24.2 | 1.0 | 470 | 7.9 | 14.2 |
|  | 3.18 | 24+ | 0 | Severe | — | — | 3.7 | — | — | 8.2 | 13.6 |
|  | 6.77 | 23+ | 0 | Severe | — | — | 4.5 | — | — | 7.6 | 15.4 |

TABLE 1-continued
Effects of TD-1123 on Various Characteristics of Upland Cotton

| Treatment | Rate (lbs/Acre) | # Days 100% Male Sterile | 100% Male Sterile + Female Fertile | Leaf Phyto. | % Set | % Seed Emerg. | Avg. # Flowers/ Plot | Grams Per Boll | Bolls Per Lb. | Seed Index | Seeds Per Boll |
|---|---|---|---|---|---|---|---|---|---|---|---|
| | 11.78 | 24+ | 0 | Severe | — | — | 1.4 | — | — | 5.6 | 11.6 |

TABLE 2
Effects of TD-1123 on Various Characteristics of Upland Cotton

| Treatment | Rate (lbs/Acre) | Plant Height (cm) | | Node Number (No.) | | Flower Counts (No.) | | Total Dry Weights (grams) | | Number of Squares (No.) | |
|---|---|---|---|---|---|---|---|---|---|---|---|
| | | 7-16 | 8-6 | 7-16 | 8-6 | 7-27 | 8-3 | 7-16 | 8-6 | 7-16 | 8-6 |
| Control | 0 | 89.7 | 113.3 | 18.7 | 24.7 | 94 | 81 | 97.3 | 198.3 | 52.3 | 26.3 |
| Dalapon | 1.73 | 86.3 | 116.0 | 18.7 | 25.0 | 56 | 56 | 77.0 | 127.3 | 42.7 | 43.3 |
| | 2.64 | — | — | — | — | 47 | 60 | — | — | — | — |
| | 6.09 | 91.7 | 120.0 | 20.3 | 24.0 | 22 | 14 | 113.7 | 151.2 | 55.7 | 36.7 |
| | 12.69 | 75.0 | 98.0 | 17.3 | 21.3 | 6 | 16 | 61.6 | 136.7 | 35.0 | 25.7 |
| TD-1123 | 0.04 | 94.0 | 109.3 | 19.7 | 26.3 | 82 | 71 | 91.6 | 208.8 | 59.0 | 76.3 |
| | 0.09 | — | — | — | — | 74 | 88 | — | — | — | — |
| | 0.17 | — | — | — | — | 73 | 103 | — | — | — | — |
| | 0.42 | — | — | — | — | 81 | 108 | — | — | — | — |
| | 0.65 | 88.7 | 117.0 | 19.0 | 26.3 | 68 | 145 | 99.0 | 180.8 | 56.7 | 73.3 |
| | 0.81 | — | — | — | — | 67 | 119 | — | — | — | — |
| | 1.07 | — | 109.0 | — | 25.3 | 57 | 140 | — | 108.4 | — | 69.3 |
| | 1.10 | — | — | — | — | 44 | 138 | — | — | — | — |
| | 1.46 | — | — | — | — | 48 | 168 | — | — | — | — |
| | 1.47 | 83.3 | 100.3 | 18.3 | 25.3 | 40 | 119 | 90.8 | 102.1 | 31.7 | 58.0 |
| | 1.52 | — | — | — | — | 27 | 118 | — | — | — | — |
| | 3.00 | — | — | — | — | 8 | 40 | — | — | — | — |
| | 3.18 | — | — | — | — | 2 | 5 | — | — | — | — |
| | 6.77 | — | — | — | — | 0 | 9 | — | — | — | — |
| | 11.78 | 69.3 | 61.7 | 15.3 | 18.7 | 0 | 3 | 58.8 | 58.0 | 1.3 | 2.1 |

| Treatment | Rate (lbs/Acre) | Number Mature Bolls (no.) | | Green Boll Weight (g) | | Square Weight (g) | | Leaf Weight (g) | | Stem Weight (g) | | Root Weight (g) | |
|---|---|---|---|---|---|---|---|---|---|---|---|---|---|
| | | 7-16 | 8-6 | 7-16 | 8-6 | 7-16 | 8-6 | 7-16 | 8-6 | 7-16 | 8-6 | 7-16 | 8-6 |
| Control | 0 | 5.7 | 27.0 | 8.5 | 87.8 | 5.6 | 3.7 | 38.0 | 41.8 | 38.2 | 58.0 | 6.8 | 7.0 |
| Dalapon | 1.73 | 6.3 | 9.7 | 6.3 | 25.5 | 5.5 | 6.0 | 28.6 | 35.6 | 30.9 | 53.0 | 5.7 | 7.2 |
| | 2.64 | — | — | — | — | — | — | — | — | — | — | — | — |
| | 6.09 | 6.3 | 6.7 | 10.7 | 11.8 | 7.0 | 3.6 | 40.9 | 59.0 | 47.6 | 67.1 | 7.5 | 9.7 |
| | 12.69 | 3.3 | 7.3 | 2.9 | 22.4 | 3.8 | 2.7 | 23.7 | 44.3 | 26.1 | 57.7 | 5.1 | 9.7 |
| TD-1123 | 0.04 | 7.7 | 18.0 | 5.6 | 56.8 | 7.1 | 10.0 | 34.4 | 56.5 | 38.3 | 74.3 | 6.2 | 11.2 |
| | 0.09 | — | — | — | — | — | — | — | — | — | — | — | — |
| | 0.17 | — | — | — | — | — | — | — | — | — | — | — | — |
| | 0.43 | — | — | — | — | — | — | — | — | — | — | — | — |
| | 0.65 | 5.7 | 14.7 | 10.4 | 39.1 | 6.8 | 8.9 | 36.1 | 49.7 | 38.7 | 72.4 | 7.0 | 10.8 |
| | 0.81 | — | — | — | — | — | — | — | — | — | — | — | — |
| | 1.07 | — | 4.0 | — | 7.7 | — | 8.1 | — | 35.5 | — | 48.7 | — | 8.4 |
| | 1.10 | — | — | — | — | — | — | — | — | — | — | — | — |
| | 1.46 | — | — | — | — | — | — | — | — | — | — | — | — |
| | 1.47 | 2.7 | 2.7 | 5.7 | 6.9 | 3.6 | 6.4 | 34.1 | 34.5 | 39.6 | 45.6 | 7.8 | 8.8 |
| | 1.52 | — | — | — | — | — | — | — | — | — | — | — | — |
| | 3.00 | — | — | — | — | — | — | — | — | — | — | — | — |
| | 3.18 | — | — | — | — | — | — | — | — | — | — | — | — |
| | 6.77 | — | — | — | — | — | — | — | — | — | — | — | — |
| | 11.78 | 1.0 | 2.0 | 1.3 | 3.1 | 0.2 | 0.6 | 22.5 | 18.1 | 28.5 | 28.7 | 6.3 | 7.5 |

The foregoing description is intended as illustrative only and is not to be construed as limiting.

What is claimed is:

1. A method of rendering cotton plants male sterile while retaining substantial female fertility comprising: providing isothiazole plant growth regulator to the plants in an amount effective to render the cotton plants male sterile while retaining substantial female fertility, including the steps of:
   contacting said plants with a preselected amount of the isothiazole plant growth regulator;
   monitoring the presence or absence and degree of burning of the bracts of the plants; and adjusting the amount of regulator in response to said monitoring.

2. The method of claim 1 wherein said adjusting comprises either:
   the application of additional regulator, or
   irrigating the plants.

3. The method of claim 1 wherein said contacting is in an amount of from about 0.1 to about 2.0 pounds per acre.

4. The method of claim 1 wherein said adjusting results in finger burning of said bracts.

5. The method of claims 1, 2, 3, or 4 wherein said regulator is an isothiazole-5-carboxylate.

6. The method of claim 1, 2, 3 or 4 wherein said regulator is potassium of 3,4-dichloroisothiazole-5-carboxylate.

7. A method of rendering cotton plants male sterile while retaining substantial female fertility comprising:
providing isothiazole plant growth regulator to the plants in an amount effective to render the cotton plants male sterile while retaining substantial female fertility, including the steps of:
contacting said plants with a preselected amount of the isothiazole plant growth regulator;
monitoring the presence or absence and degree of burning of the bracts of the plant; and
in response to said monitoring, either;
further contacting said plants with an additional amount of plant growth regulator or
irrigating the plants or
maintaining said contacting.

8. The method of claim 7 wherein said preselected amount is from about 0.1 to about 2.0 pounds per acre.

9. The method of claim 7 wherein said amount is preselected to result in bract finger burning in said plants in from about 3 to about 5 days.

10. The method of claim 7 wherein said further contacting is in response to a monitored condition of no burning of the bracts and said irrigation is in response to a condition of excessive burning of the bracts.

11. The method of claim 7, 8, 9 or 10 wherein said regulator is an isothiazole-5-carboxylate.

12. The method of claim 7, 8, 9 or 10 wherein said isothiazole is a potassium of 3,4,-dichloroisothiazole-5-carboxylate.

13. A method for rendering cotton plants male sterile for substantially an entire growing season comprising:
providing isothiazole plant growth regulator to the cotton plants in an amount effective to render the cotton plants male sterile while retaining substantial female fertility for substantially an entire growing season, including the steps of:
periodically applying to the plants preselected amounts of isothiazole plant growth regulator
monitoring the presence or absence and degree of burning of the bracts of the plant; and
adjusting the amount and/or periodicity of application of said regulator in response to said monitoring, the periodic application commencing at least about two weeks prior to the first flowering of said plants in said season and continuing at least until about twelve weeks prior to harvest of the plants.

14. The method of claim 13 wherein said adjusting results in finger burning of said bracts.

15. The method of claim 13 wherein said application is in the amount of from about 0.1 to about 2.0 pounds per acre.

16. The method of claim 13, 14, or 15 wherein said regulator is an isothiazole-5-carboxylate.

17. The method of claim 13, 14 or 15 wherein said regulator is a potassium 3,4-dichloroisothiazole-5-carboxylate.

18. A method for achieving male sterility in cotton plants comprising:
applying in a first application to said cotton plants an amount of an isothiazole plant growth regulator sufficient to cause finger burning of the bracts of said cotton plants but which is not so much as to cause excessive burning thereof; and
periodically applying additional amounts of said regulator to said plants sufficient to maintain finger burning without achieving excessive burning of the bracts.

19. The method of claim 18 wherein said period is about two weeks.

20. The method of claim 18 wherein said first application is about two weeks prior to first flowering of the plants.

21. The method of claim 18, 19 or 20 wherein said regulator is an isothiazole-5-carboxylate.

22. The method of claim 18, 19 or 20 wherein said regulator is a potassium 3,4-dichloroisothiazole-5-carboxylate.

* * * * *